US009429160B2

(12) United States Patent
Tanaka et al.

(10) Patent No.: US 9,429,160 B2
(45) Date of Patent: Aug. 30, 2016

(54) CENTRIFUGAL PUMP AND METHOD OF MANUFACTURING CENTRIFUGAL PUMP

(71) Applicant: TERUMO KABUSHIKI KAISHA, Tokyo (JP)

(72) Inventors: Shotaro Tanaka, Kanagawa (JP); Koko Kumano, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 692 days.

(21) Appl. No.: 13/832,244

(22) Filed: Mar. 15, 2013

(65) Prior Publication Data

US 2013/0251516 A1 Sep. 26, 2013

(30) Foreign Application Priority Data

Mar. 23, 2012 (JP) ................................ 2012-068398

(51) Int. Cl.

| | |
|---|---|
| ***F04D 1/00*** | (2006.01) |
| ***A61M 1/10*** | (2006.01) |
| ***A61M 1/00*** | (2006.01) |
| ***F04D 29/22*** | (2006.01) |

(52) U.S. Cl.

CPC ............ *F04D 1/00* (2013.01); *F04D 29/2227* (2013.01); *F05D 2230/20* (2013.01); *F05D 2230/21* (2013.01); *Y10T 29/49243* (2015.01)

(58) Field of Classification Search

CPC ............................ A61M 1/10; A61M 1/1012

USPC ......................................................... 415/203

See application file for complete search history.

(56) References Cited

U.S. PATENT DOCUMENTS

| | | | | |
|---|---|---|---|---|
| 2,095,055 A * | 10/1937 | Campbell | B22D 19/00 | 164/111 |
| 4,936,759 A * | 6/1990 | Clausen | A61M 1/101 | 128/DIG. 3 |
| 5,441,535 A | 8/1995 | Takahashi et al. | | |
| 5,575,630 A | 11/1996 | Nakazawa et al. | | |
| 5,601,418 A | 2/1997 | Ohara et al. | | |
| 5,658,136 A | 8/1997 | Mendler | | |
| 5,683,231 A * | 11/1997 | Nakazawa | A61M 1/101 | 415/900 |
| 5,707,218 A | 1/1998 | Maher et al. | | |
| 5,746,575 A | 5/1998 | Westphal et al. | | |
| 5,803,720 A | 9/1998 | Ohara et al. | | |
| 5,863,179 A | 1/1999 | Westphal et al. | | |
| 6,015,434 A | 1/2000 | Yamane | | |
| 6,071,093 A | 6/2000 | Hart | | |
| 6,135,710 A | 10/2000 | Araki et al. | | |
| 6,171,078 B1 | 1/2001 | Schob | | |
| 6,183,220 B1 * | 2/2001 | Ohara | A61M 1/101 | 415/206 |
| 6,227,797 B1 | 5/2001 | Watterson et al. | | |
| 6,250,880 B1 | 6/2001 | Woodard et al. | | |

(Continued)

*Primary Examiner* — Mary A Davis
*Assistant Examiner* — Anthony Ayala Delgado
(74) *Attorney, Agent, or Firm* — Gael Diane Tisack; Darryl Newell; MacMillan, Sobanski & Todd, LLC

(57) ABSTRACT

A centrifugal blood pump reliably prevents blood from entering between an impeller and a shaft member. Pump 1 includes a pump chamber 24, a housing 2 including a blood inlet 25 and a blood outlet 26, an impeller 3 as a centrifugal force applying member rotatably encased in the pump chamber 24 and applying a centrifugal force to the blood Q by the rotation of the impeller 3. A support mechanism 4 supports impeller 3 rotatably with respect to the housing 2. The support mechanism 4 includes a rod-shaped shaft member 41 disposed at the rotation center of the impeller 3. Shaft member 41 and the impeller 3 are formed integrally with each other, as by insert molding.

9 Claims, 10 Drawing Sheets

(56) References Cited

U.S. PATENT DOCUMENTS

| | | | |
|---|---|---|---|
| 6,293,752 | B1 | 9/2001 | Clague et al. |
| 6,589,031 | B2 | 7/2003 | Maeda et al. |
| 6,609,883 | B2 | 8/2003 | Woodard et al. |
| 6,638,011 | B2 | 10/2003 | Woodard et al. |
| 6,722,863 | B2 | 4/2004 | Maeda et al. |
| 6,824,358 | B2 | 11/2004 | Araki et al. |
| 6,966,748 | B2 | 11/2005 | Woodard et al. |

* cited by examiner

1
Q
26
33
362
36
3
35
351
364
32
31
25
363
34
361
12
60
254
421
413
42(4)
411
41(4)
414
412
221
43(4)
431
11
364
362
21
24
22
33
232
241
23
231
27
29
28
2

CENTRIFUGAL PUMP AND METHOD OF MANUFACTURING CENTRIFUGAL PUMP

CROSS REFERENCE TO RELATED APPLICATIONS

This application claims priority to Japanese patent application 2012-068398, filed Mar. 23, 2012, which is hereby incorporated by reference.

STATEMENT REGARDING FEDERALLY SPONSORED RESEARCH

Not Applicable.

BACKGROUND OF THE INVENTION

1. Technical Field

The present invention relates to a centrifugal pump and a method of manufacturing a centrifugal pump.

2. Background Art

In the prior art, a blood pump for transporting blood includes a turbo-type pump for delivering blood by a centrifugal force, the pump being provided with a hollow housing, an impeller rotatably encased in the housing, and a rotation shaft being in the rotation center of the impeller (for example, see U.S. Pat. No. 5,575,630). In the blood pump disclosed in U.S. Pat. No. 5,575,630, the housing, the impeller, and the rotation shaft are constituted of separate members which are assembled to manufacture the blood pump. In assembling the blood pump, the rotation shaft and a magnet are first assembled onto the pre-existing impeller, and then the assembled components are encased in the housing. At least one of the rotation shaft or a pivot bearing that receives the shaft is made of a relatively hard material such as metal or ceramic in order to provide sufficient durability to the constant wear that occurs during rotation of the impeller.

Desirable properties of the impeller include compatibility with blood, easy moldability, and transparency. Due to these different considerations, the preferred materials for the impeller are different from the preferred materials for the shaft member. Consequently, the two components have been separately fabricated and then assembled together.

Since the blood pump disclosed in U.S. Pat. No. 5,575,630 has a structure in which the rotation shaft is assembled to the impeller by inserting it into a pre-existing bore formed in the impeller, a slight (minute) gap is unavoidably present between the rotation shaft and the impeller because of manufacturing tolerances and the requirement to make the shaft member insertable. During the use of the blood pump, blood enters into the gap between the rotation shaft and the impeller due to a capillary phenomenon or a pressure difference, which can result in blood clotting and hemolysis during pump operation.

SUMMARY OF THE INVENTION

The invention provides a centrifugal pump, which reliably prevents blood from entering between a centrifugal force applying member and a shaft member, and a method of manufacturing the centrifugal pump.

According to the present invention, a shaft member and a centrifugal force applying member (i.e., impeller) are formed integrally with each other. Consequently, it is possible to prevent a gap from being formed between the centrifugal force applying member and the shaft member, that is, at a boundary portion between the centrifugal force applying member and the shaft member. Blood flowing into a housing through a blood inlet is prevented from entering the boundary portion, and thus it is possible to prevent blood clotting and hemolysis at the boundary portion during the use of the centrifugal pump.

DETAILED DESCRIPTION OF PREFERRED EMBODIMENTS

Hereinafter, a centrifugal pump and a method of manufacturing a centrifugal pump according to the invention will be described in detail based on preferred embodiments shown in the accompanying drawings.

FIGS. 1 to 7 are vertical cross-sectional views sequentially showing a method of manufacturing a centrifugal pump according to a first embodiment of the invention. In the following description, the upper sides of FIGS. 1 to 10 will be referred to as “upper” and their lower sides as “lower” for convenience of explanation.

Figure 7:
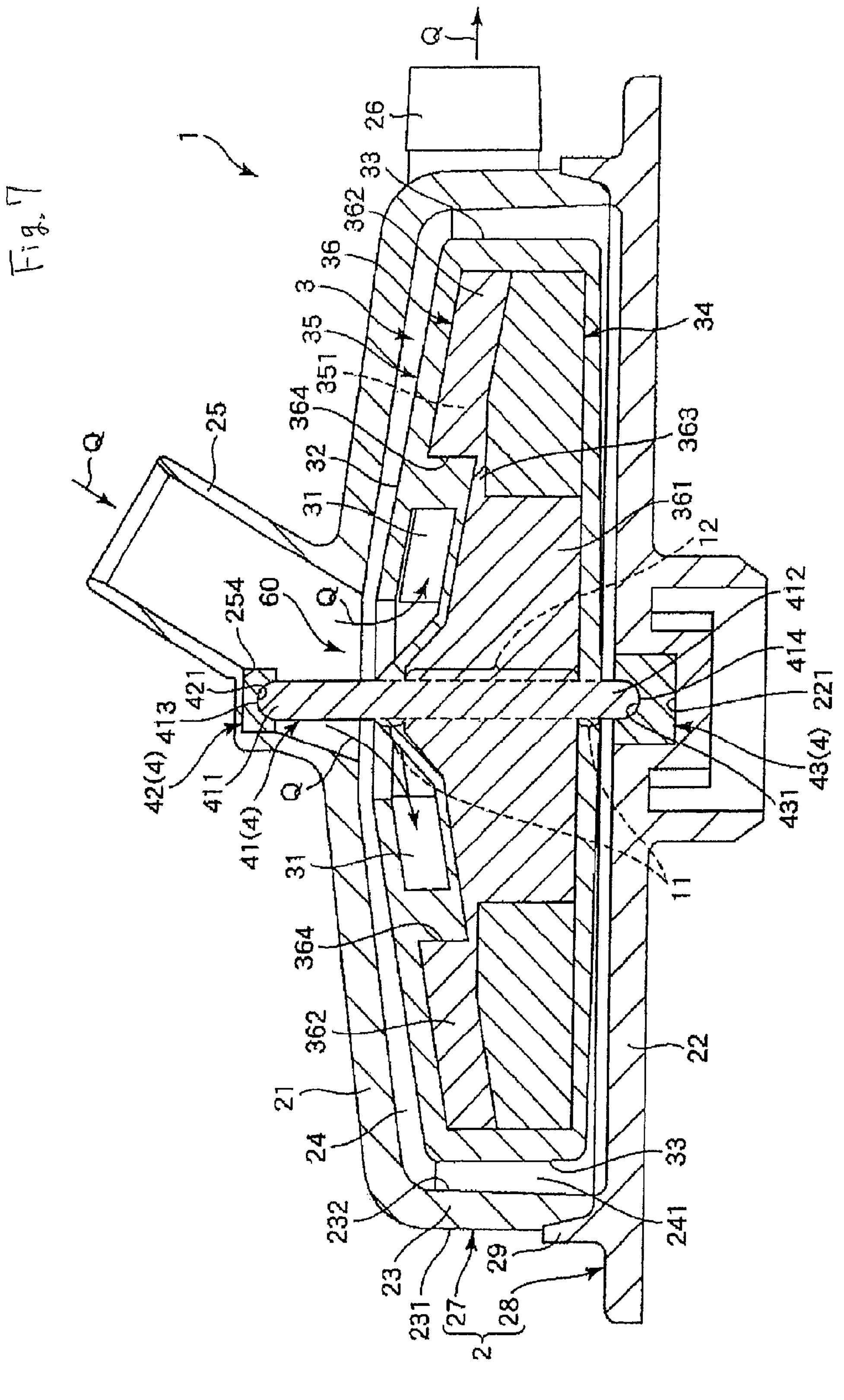
FIG. 7 is a vertical cross-sectional view showing an assembled blood pump according to a first embodiment.

A centrifugal pump 1 shown in FIG. 7 is provided with a housing 2 constituted of a hollow body, an impeller 3 rotatably encased in the housing 2, and a support mechanism 4 supporting the impeller 3 rotatably with respect to the housing 2. Hereinafter, the configuration of each component will be described.

The overall shape of the housing 2 is a flat cylindrical shape and is constituted of an upper member 27 and a lower member 28. The upper member 27 has a top plate 21 and a side wall 23 provided at an edge of the top plate 21 so as to have an annular shape in a circumferential direction of the top plate 21. The lower member 28 has a bottom plate 22 and a rib 29 provided near the edge of the top plate 21 so as to have an annular shape in the circumferential direction of the top plate 21. The rib 29 is fitted in a liquid-tight manner to the side wall 23 onto its outer periphery, whereby the upper member 27 and the lower member 28 are assembled. A flat space surrounded by the top plate 21, the bottom plate 22, and the side wall 23 defines a pump chamber 24.

The housing 2 has a blood inlet 25 through which blood Q flows in and a blood outlet 26 through which the blood Q flows out. The blood inlet 25 and the blood outlet 26 each communicate with the pump chamber 24. The blood Q flowing in through the blood inlet 25 can flow out through the blood outlet 26 via the pump chamber 24.

The blood inlet 25 is formed to protrude in a tubular form from the central portion of the top plate 21 of the upper member 27. A tube constituting a blood circuit of a perfusion system can be connected to the blood inlet 25, for example.

The blood outlet 26 is formed to protrude in a tubular form from an outer periphery 231 of the side wall 23. The blood outlet 26 extends in a tangential direction from the outer periphery 231 of the side wall 23.

In the pump chamber 24 of the housing 2, the disk-shaped impeller 3 is disposed concentrically. The impeller 3 is a centrifugal force applying member which rotates to apply the centrifugal force to the blood Q.

The impeller 3 has a cover member 35, a spacer member 36 encased in the cover member 35, and a magnet 34 encased in the cover member 35 along with the spacer member 36.

The cover member 35 consists of a disk-shaped hollow body having a hollow 351 which can collectively encase the spacer member 36 and the magnet 34 together.

Figure 10:
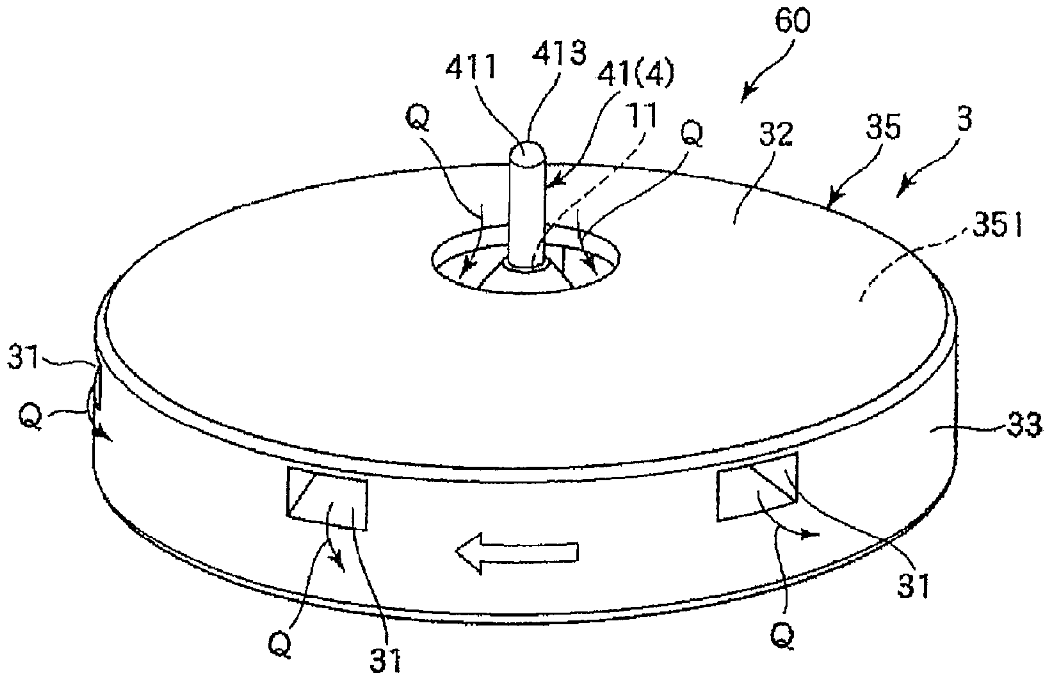
FIG. 10 is a perspective view of the state shown in FIG. 6.

As shown in FIG. 10, the impeller formed by cover member 35 and spacer member 36 has a plurality of blood flow paths 31 (e.g., six in this embodiment) through which the blood Q passes. The blood flow paths 31 are radially formed beginning at the center of the cover member 35. The respective portions of the blood flow paths 31 on the center side of the cover member 35 are joined to (intersected with) each other and open in the upper surface 32 of the cover member 35. Meanwhile, the respective portions of the blood flow paths 31 on the opposite side to the center side of the cover member 35 open in an outer periphery 33 of the cover member 35. A gap 241 is formed between the outer periphery 33 of the cover member 35 and an inner periphery 232 of the side wall 23 of the housing 2 (FIG. 7).

When the cover member 35 rotates in a clockwise direction in FIG. 10, the blood Q flowing in through the blood inlet 25 enters each of the blood flow paths 31 from the center side portion of the cover member 35 to receive a centrifugal force, and, thus, to flow down in the blood flow paths 31. The blood Q, which has flowed down, flows out into the gap 241. Then, when the blood Q receives rotational force in the clockwise direction in the gap 241 and reaches the blood outlet 26, the blood Q is discharged from the blood outlet 26.

Figure 8:
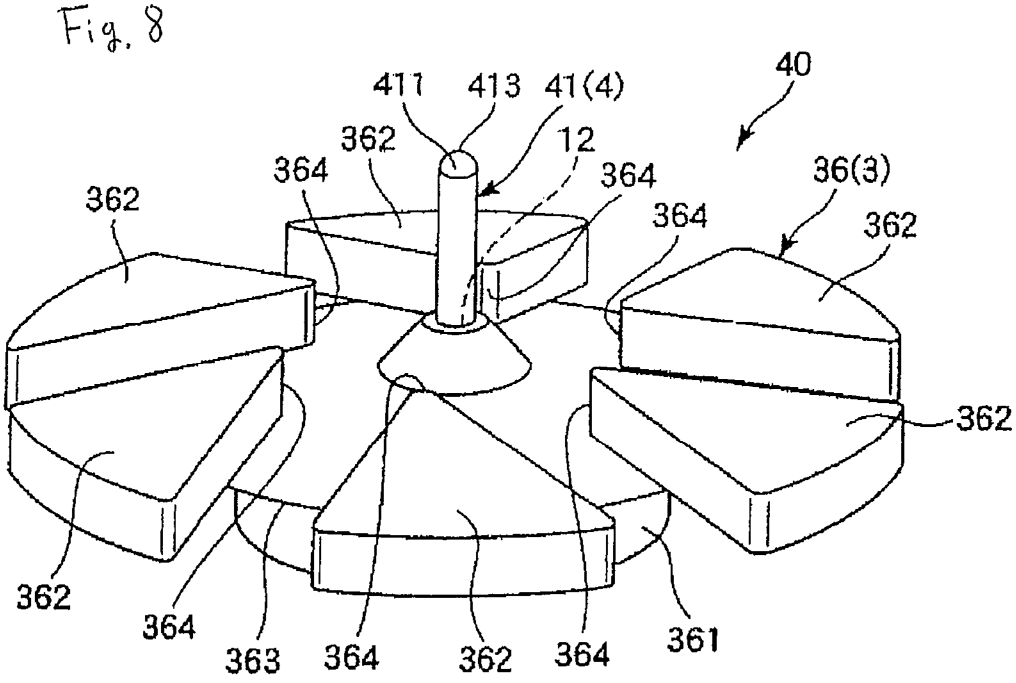
FIG. 8 is a perspective view of a state shown in FIG. 3.
Figure 9:
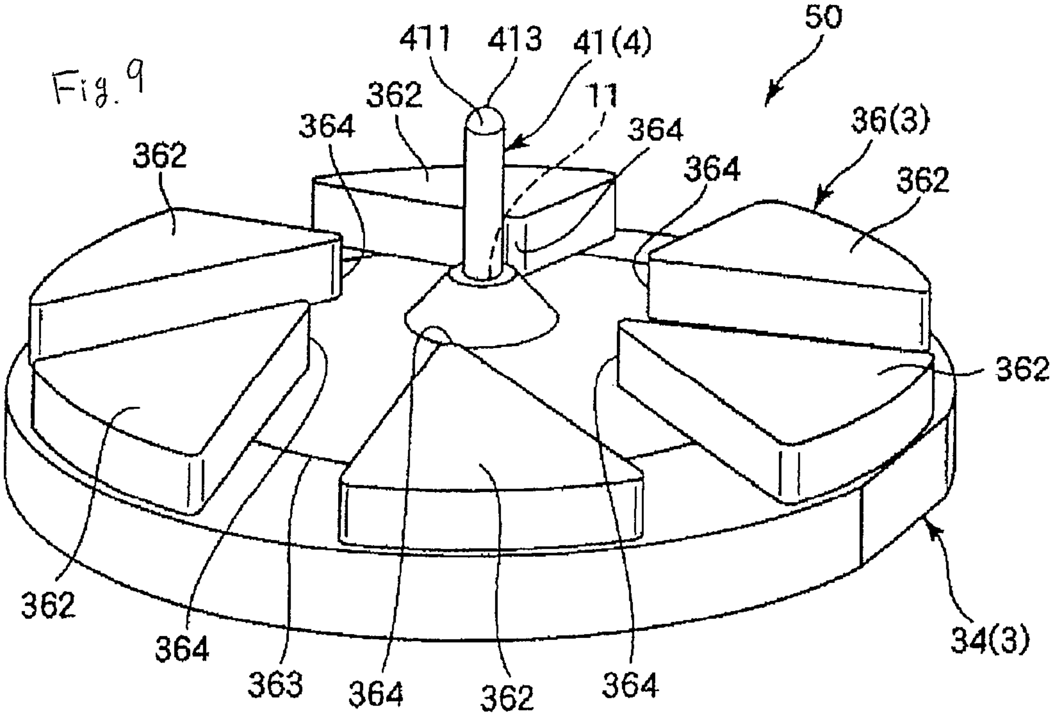
FIG. 9 is a perspective view of a state shown in FIG. 4.

The spacer member 36 is disposed in the hollow 351 of the cover member 35. As shown in FIGS. 8 and 9, the spacer member 36 has a disk-shaped base 361, a plurality of fan-shaped portions 362 (six in the illustrated configuration) arranged above the base 361 and having a fan shape in plan view, and an annular connection 363 connecting the base 361 and each of the fan-shaped portions 362.

Fan-shaped portions 362 have corners 364, each with a central angle facing toward the center of the base 361 and arranged at equal angular intervals around the central axis of the base 361. The fan-shaped portions 362 adjacent to each other are spaced apart from each other, and the single blood flow path 31 is constituted between the fan-shaped portions 362.

Figure 6:
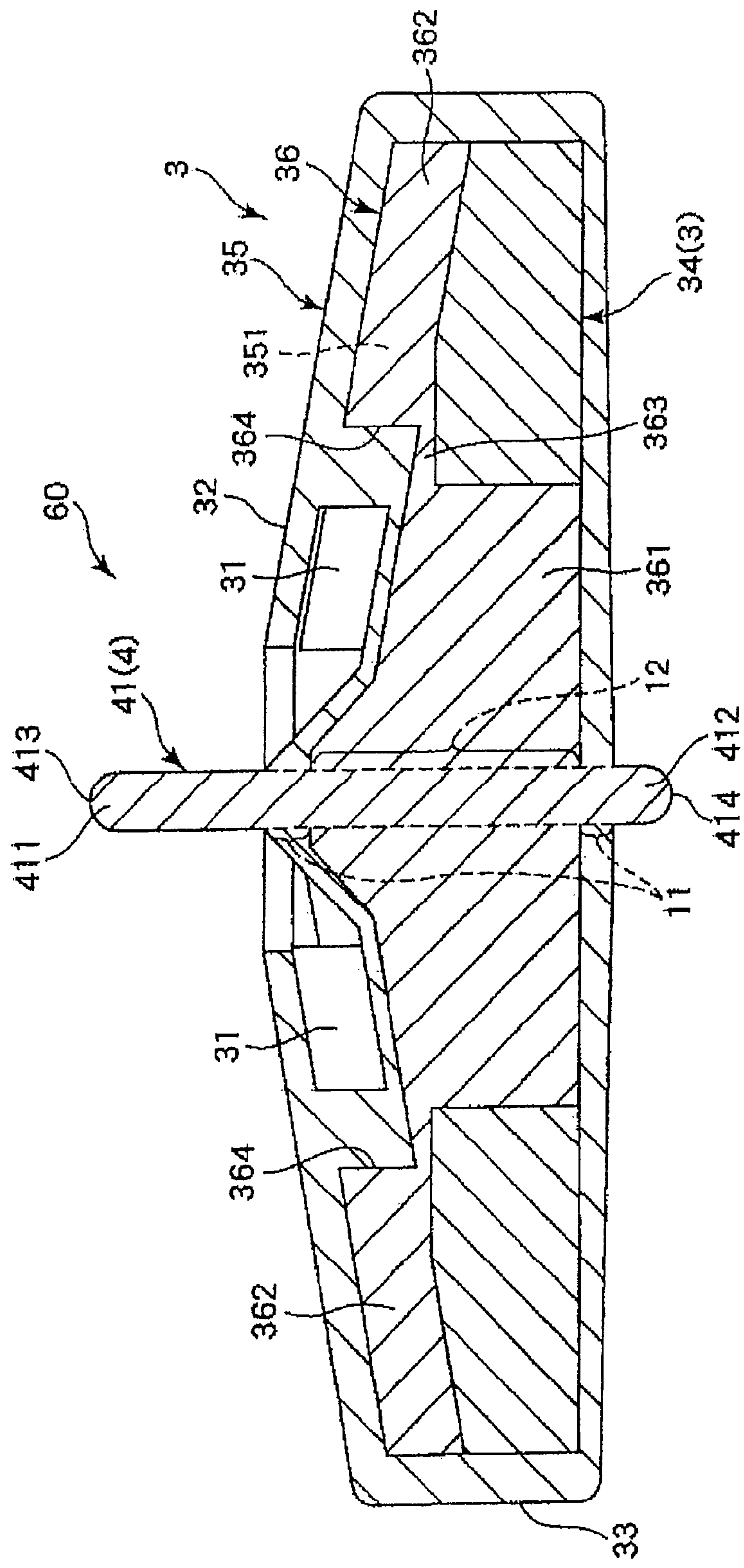
FIG. 6 is a vertical cross-sectional view showing the product resulting from FIG. 5.

As shown in FIGS. 6, 7, and 9, the annular magnet 34 is mounted between the base 361 and each of the fan-shaped portions 362 of the spacer member 36 by press fitting, for example. In the mounted state, the magnet 34 fills the entire hollow 351 of the cover member 35 in cooperation with the spacer member 36.

For operating the centrifugal pump 1, the centrifugal pump is first installed in external driving means (not shown). The external driving means has, for example, a motor and a permanent magnet connected to the motor, and the permanent magnet attracts the magnet 34 built in the centrifugal pump 1 by a magnetic force. When the motor rotates in this state, the rotational force is transmitted through the magnets attracted to each other, whereby the impeller 3 can be rotated in the housing 2.

Although the diameter of the impeller 3 is not particularly limited, the diameter may preferably be from 20 to 200 mm, for example, and more preferably 30 to 100 mm. Although the thickness of the impeller 3 is not particularly limited, the thickness may preferably be from 3 to 40 mm, for example, and more preferably 5 to 30 mm. Although a maximum rotation speed of the impeller 3 is not particularly limited, the rotation speed may preferably be up to about 2000 to 6000 rpm, and more preferably 2500 to 5000 rpm, for example.

Although materials for the cover member 35, the spacer member 36, and the housing 2 are not particularly limited, polycarbonate and acrylic resin are preferably used since these resins are excellent in compatibility with blood Q, transparency, and moldability.

As shown in FIG. 7, the impeller 3 is supported rotatably with respect to the housing 2 through the support mechanism 4. The support mechanism 4 has a shaft member 41 constituted of a rod-shaped body, a first bearing 42 rotatably supporting an upper end (one end) portion 411 of the shaft member 41, and a second bearing 43 rotatably supporting a lower end (the other end) portion 412 of the shaft member 41. The shaft member 41 is installed so as to be inserted through the center rotation axis of the impeller 3. The first bearing 42 is installed in and fixed to a first bearing installation portion 254 recessed in the inner peripheral portion of the blood inlet 25 of the housing 2. The second bearing 43 is installed in and fixed to a position different from the position of the first bearing installation portion 254 (first bearing 42) of the housing 2, that is, a second bearing installation portion 221 recessed in the central portion of the bottom plate 22. Although a method of fixing the first and second bearings 42 and 43 to the housing 2 is not particularly limited, there are, for example, a method using press fitting, a method using adhesion (with an adhesive or a solvent), a method using fusion bonding (such as thermal fusion bonding, high-frequency fusion bonding, and ultrasonic fusion bonding), and a method using insert molding.

Because of their contact with rotating shaft member 41, first and second bearings 42 and 43 are preferably formed of a material having a higher hardness and resistance to wear than the material forming impeller 3 and housing 2.

The shaft member 41 is a solid body having a constant outer diameter in the longitudinal direction. The upper end surface 413 and the lower end surface 414 of the shaft member 41 are rounded and have a semi-spherical shape. In the shaft member 41, at least the upper end surface 413 and the lower end surface 414 may be coated with diamond-like carbon (DLC) or titanium, for example.

In the centrifugal pump 1 shown in FIG. 7, the cover member 35 and the spacer member 36 are formed integrally with the shaft member 41. According to this construction, it is possible to prevent a gap from being formed between the cover member 35 and the shaft member 41, that is, at the boundary portion 11. It is also possible to prevent a gap from being formed between the spacer member 36 and the shaft member 41, that is, at the boundary portion 12. It is further possible to prevent the blood Q in the pump chamber 24 from entering the boundary portions 11 and 12 and prevent clotting of the blood Q and hemolysis at the boundary portions 11 and 12 during the use of the centrifugal pump 1.

The integral formation of the cover member 35 and the shaft member 41 and the integral formation of the spacer member 36 and the shaft member 41 can be realized by insert molding as described below. By using the technique of insert molding, members can be integrally molded, and thus it is possible to prevent the blood Q from entering into a spacing and prevent or suppress occurrence of thrombus and hemolysis. Because of the unitary structure of the integrally formed impeller and shaft member, a gap between members is not formed. Since blood cannot enter between the members, sterilization before molding can be omitted.

The first bearing 42 is constituted of a cup-shaped member having a semi-spherical concave 421. The upper end surface 413 of the shaft member 41 can slide on the concave 421.

Similarly to the first bearing 42, the second bearing 43 is constituted of a cup-shaped member having a semi-spherical concave 431. The lower end surface 414 of the shaft member 41 can slide on the concave 431.

In a preferred embodiment, the shaft member 41 is made of a metal material, and the first and second bearings 42 and 43 are each made of a resin material.

The metal material is not particularly limited and includes, for example, stainless steel. In addition to the metal material, ceramics or the like may be used. The hardness (Vickers hardness, Hv) of such metal or ceramic material is not particularly limited, and may preferably be not less than about 50 and more preferably not less than about 100, for example.

The resin material for bearings 42 and 43 is not particularly limited and may include a thermoplastic resin, for example. As the thermoplastic resin, ultrahigh molecular weight polyethylene and polypropylene can be used, for example.

Next, a method of manufacturing the centrifugal pump 1 by assembling the housing 2, the impeller 3, and the support mechanism 4, namely by encasing the impeller 3 and the support mechanism 4 in the housing 2 will be described with reference to FIGS. 1 to 7. The manufacturing method is characterized in that the shaft member 41 and the impeller 3 are formed integrally with each other before the impeller 3 and the support mechanism 4 are encased in the housing 2.

Prior to the description of the manufacturing method, a molding die 20 for molding the spacer member (FIG. 2) and a molding die 30 for molding the cover member 30 (FIG. 5) that are used in the manufacturing process will be described.

Figure 2:
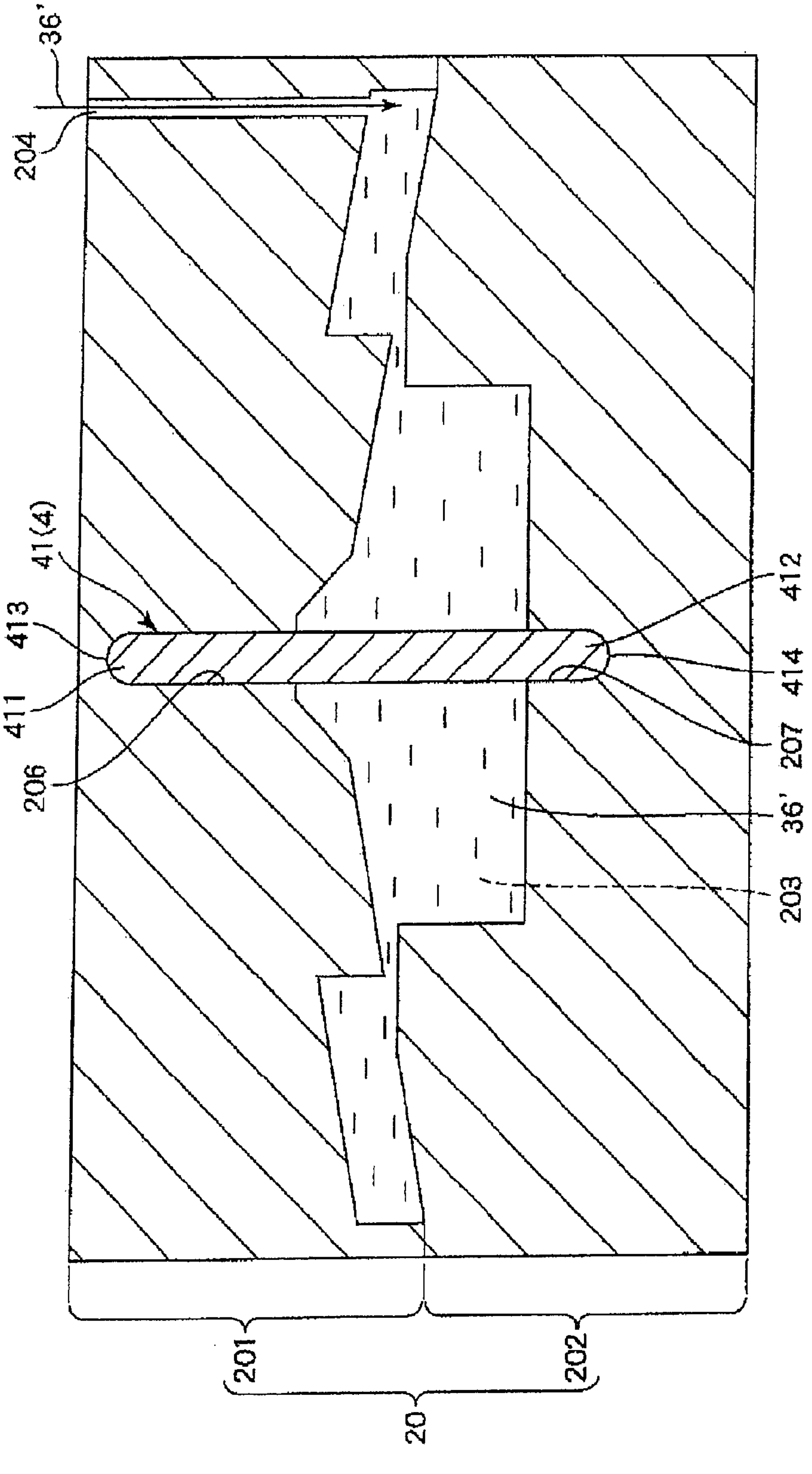
FIG. 2 is a vertical cross-sectional view showing the shaft member in a die during insert molding of a spacer member of an impeller.

As shown in FIG. 2, the molding die 20 is used for molding the spacer member 36. The molding die 20 has an upper molding die 201 and a lower molding die 202 so that they can be vertically opened and closed. When the upper molding die 201 and the lower molding die 202 are closed, a cavity 203 for molding the spacer member 36 can be formed. The upper molding die 201 has a communication hole 204 communicating with the cavity 203. The cavity 203 can be filled with a resin material 36' as a constituent material of the spacer member 36 in the liquid state through the communication hole 204. The resin material 36' is cooled to become the spacer member 36.

The upper molding die 201 has a recess 206 into which an upper end side portion of the shaft member 41 is inserted, and the lower molding die 202 has a recess 207 into which a lower end side portion of the shaft member 41 is inserted. In such a state that the shaft member 41 is inserted through the recesses 206 and 207, the recesses 206 and 207 each are sealed in a liquid-tight manner.

Figure 5:
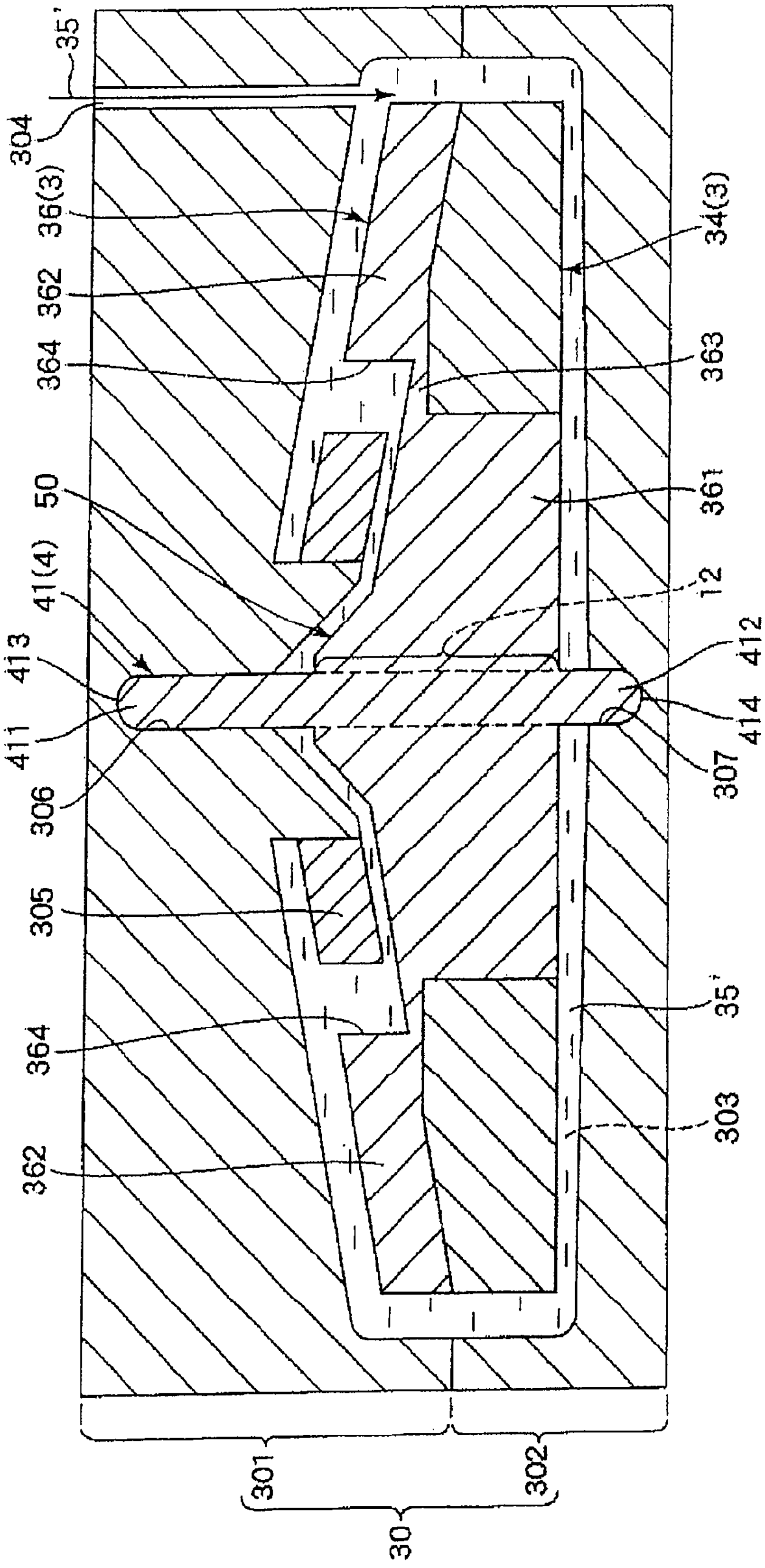
FIG. 5 is a vertical cross-sectional view showing the product of FIG. 3 in a die during insert molding of a cover member.

As shown in FIG. 5, the molding die 30 is used to form the cover member 35. The molding die 30 has an upper molding die 301 and a lower molding die 302 so that they can be vertically opened and closed. The molding die 30 further has a core 305 removably mounted on the inside of the upper molding die 301. When the upper molding die 301 on which the core 305 is mounted and the lower molding die 302 are closed, a cavity 303 for molding the cover member 35 can be formed. Core 305 corresponds to openings in cover member 35 for providing blood flow paths 31. The upper molding die 301 has a communication hole 304 communicating with the cavity 303. The cavity 303 can be filled with a resin material 35' as a constituent material of the cover member 35 in the liquid state through the communication hole 304. The resin material 35' is cooled to become the cover member 35.

The upper molding die 301 has a recess 306 into which the upper end side portion of the shaft member 41 is inserted, and the lower molding die 302 has a recess 307 into which the lower end side portion of the shaft member 41 is inserted.

Figure 1:
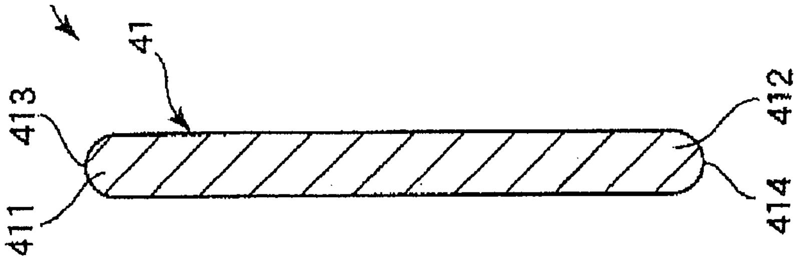
FIG. 1 is a vertical cross-sectional view showing a shaft member.

According to the sequence of the method of the invention beginning with FIG. 1, the shaft member 41 constituting the support mechanism 4 is provided.

Next, as shown in FIG. 2, the molding die 20 is provided, and the upper molding die 201 and the lower molding die 202 are brought into the mold opening state. The shaft member 41 is disposed between the upper and lower molds, and these molds are then brought into the mold closing state. Accordingly, the molding die 20 is in such a state that the shaft member 41 is disposed in the cavity 203.

Next, the entire cavity 203 is filled with the resin material 36' in the liquid state through the communication hole 204 of the upper molding die 201.

Next, the resin material 36' is cooled together with the molding die 20 low enough to solidify the resin material 36' in the cavity 203.

Figure 3:
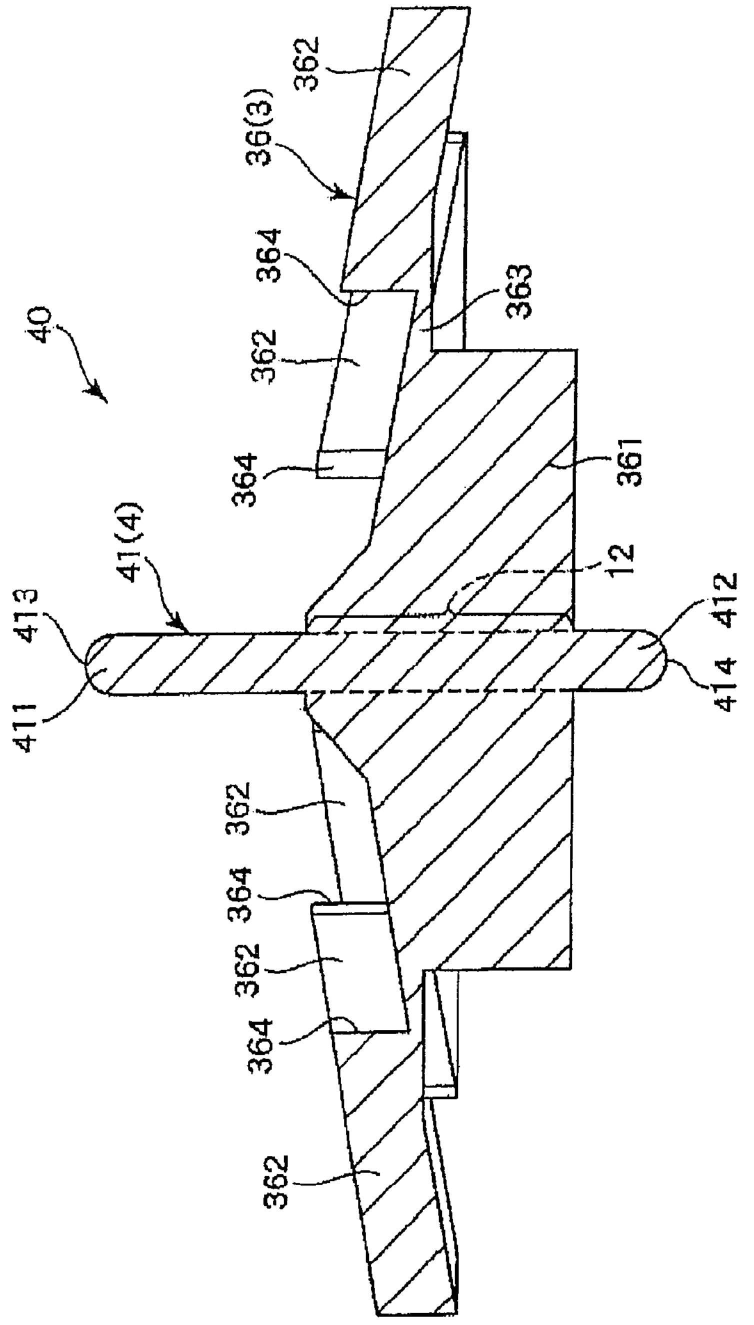
FIG. 3 is a vertical cross-sectional view showing the shaft member and spacer member after insert molding.

Next, the molding die 20 is opened, and a molded product is released from the molding die 20, whereby a molded body (first molded body) 40 molded by insert molding is obtained as shown in FIG. 3. Thus, the molded body 40 is obtained by integrally forming the spacer member 36 onto the shaft member 41.

Figure 4:
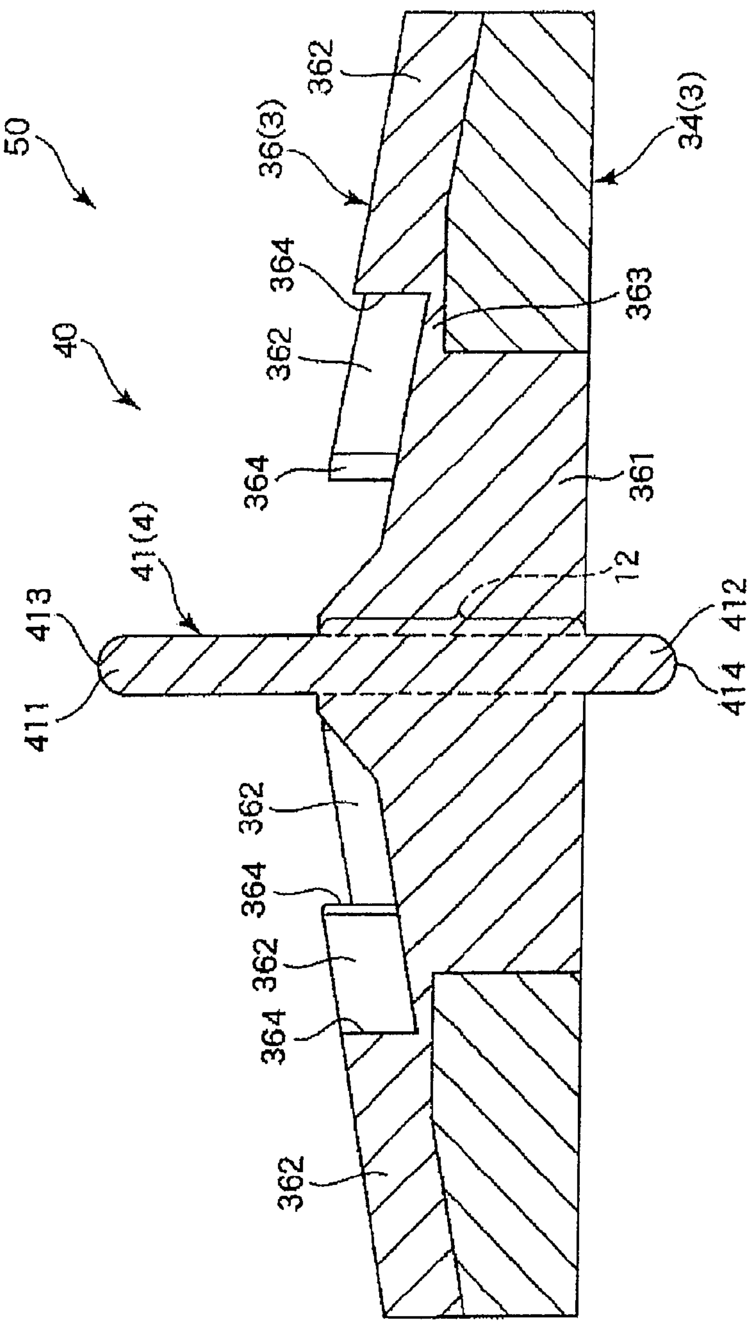
FIG. 4 is a vertical cross-sectional view showing the shaft member and spacer member after inserting magnets.

Next, as shown in FIG. 4, the magnet 34 is affixed on the spacer member 36 of the molded body 40, whereby an assembly 50 is obtained. For mounting the magnet, adhesion or press fitting is appropriately selected.

Next, as shown in FIG. 5, the molding die 30 is provided, and the upper molding die 301 mounted with the core 305 and the lower molding die 302 are brought into the mold opening state. The assembly 50 is disposed between the upper and lower molds, and these molds are then brought into the mold closing state. According to this constitution, the molding die for molding the cover member 30 is in such a state that the assembly 50 is disposed in the cavity 303.

Then, the entire cavity 303 is filled with the resin material 35' in the liquid state through the communication hole 304 of the upper molding die 301.

Next, the resin material 35' is cooled together with the molding die for molding the cover member 30 low enough to solidify the resin material 35' in the cavity 303.

Next, the molding die 30 is opened, and a molded product is released from the molding die 30, whereby a molded body (second molded body) 60 molded by insert molding is obtained as shown in FIG. 6. The molded body 60 is obtained by further integrally forming the shaft member 41 with the cover member 35.

Next, the housing 2 is provided. In the housing 2, the first and second bearings 42 and 43 each are previously fixed to the housing 2.

Then, as shown in FIG. 7, in such a state that the housing 2 is separated into the upper member 27 and the lower member 28, the molded body 60 is disposed between the upper member 27 and the lower member 28, and thereafter, the upper member 27 and the lower member 28 are connected, whereby the centrifugal pump 1 is obtained. As described above, in the centrifugal pump 1, the shaft member 41, the cover member 35, and the spacer member 36 are formed integrally with each other to prevent the blood Q from entering the boundary portions 11 and 12.

The shaft member 41 is preferably made of a metal material to obtain strength, hardness and durability. The cover member 35 and the spacer member 36 are preferably made of a resin material to obtain ease of molding. Alternatively, the shaft member 41 may be constituted of a resin material and coated with a material (metal or resin) with a greater hardness than the material used for housing 2 and impeller 3.

Figure 11:
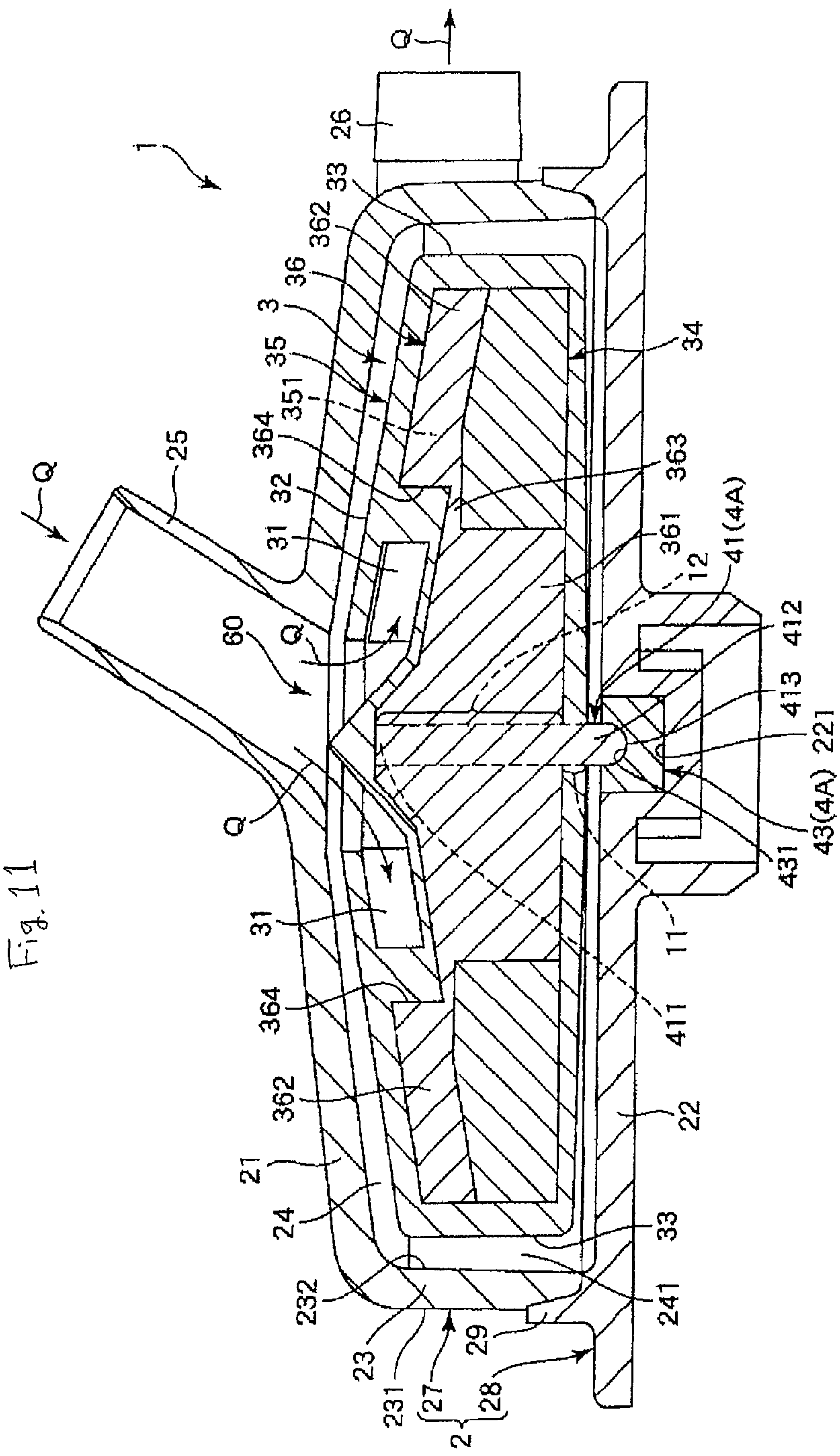
FIG. 11 is a vertical cross-sectional view showing a second embodiment of a centrifugal pump according to the invention.

FIG. 11 is a vertical cross-sectional view showing a second embodiment of a centrifugal pump according to the invention. Only the points different from the first embodiment will be described, and descriptions of similar matters will not be repeated.

The embodiment is similar to the first embodiment, except that the configuration of a support mechanism is different. In the centrifugal pump 1 of the embodiment shown in FIG. 11, a support mechanism 4A includes a second (lower) bearing 43 but lacks the first or upper bearing 42 of the previous embodiment. Shaft member 41 does not fully penetrate through impeller 3, so that its upper portion 411 is located within spacer member 36 of the impeller 3. Accordingly, the shaft member 41 is rotationally supported only on one side (the lower side), instead of being rotatably supported on the both sides (upper and lower sides) as in the first embodiment.

When the centrifugal pump 1 having the above configuration is operated, the impeller 3 can be stably rotated by its own centrifugal force.

Hereinabove, although the illustrated embodiments of the centrifugal pump and the method of manufacturing a centrifugal pump according to the invention have been described, the invention is not limited thereto, and each component constituting the centrifugal pump can be replaced with one having any configuration which can exhibit similar functions. Further, any component may be added to the centrifugal pump.

The centrifugal pump and the method of manufacturing a centrifugal pump according to the invention may be a combination of two or more arbitrary configurations of the above embodiments.

Although the shaft member is a solid body in the above embodiments, the invention is not limited thereto, and the shaft member may be a hollow body.

What is claimed is:

1. A centrifugal pump comprising:

a housing comprised of a hollow body having a blood inlet and a blood outlet, wherein the blood inlet communicates with a chamber of the hollow body for an inflow of blood, and wherein the blood outlet communicates with the chamber for an outflow of blood;

a centrifugal impeller rotatably mounted within the chamber for applying a centrifugal force to the blood in the chamber by rotation of the centrifugal impeller, wherein the centrifugal impeller is comprised of a material having a first hardness, wherein the centrifugal impeller is comprised of a spacer member defining blood flow paths, a magnet mounted in the spacer member, and a cover member disposed over the spacer member and the magnet; and a support mechanism rotatably supporting the centrifugal impeller with respect to the housing, wherein the support mechanism includes a shaft member disposed within the centrifugal impeller along a center rotation axis of the centrifugal impeller, wherein the shaft member is comprised of a material having a second hardness greater than the first hardness;

wherein the centrifugal impeller is integrally formed with the shaft member by insert molding of the spacer member and the cover member on the shaft member so that there is no interposing gap between the shaft member and the centrifugal impeller into which any blood can enter.

2. The centrifugal pump according to claim 1, wherein the shaft member has a rod shape.

3. The centrifugal pump according to claim 1, wherein the shaft member is made of a metal material and the impeller is made of a resin material.

4. The centrifugal pump according to claim 1, wherein the support mechanism further comprises a first bearing installed in the housing at a lower surface of the chamber and rotatably supporting one end of the shaft member, and a second bearing installed in the housing at an upper surface of the chamber and rotatably supporting the other end of the shaft member.

5. The centrifugal pump according to claim 1, wherein the centrifugal impeller has a disk shape and comprises a plurality of blood flow paths which are radially formed from the center of the centrifugal impeller and through which the blood passes.

6. A method of manufacturing a centrifugal pump for pumping blood, comprising the steps of:

supporting a shaft member in a first die, wherein the shaft member is comprised of a material having a first hardness;

integrally forming a spacer member of a centrifugal impeller with the shaft member by insert molding the spacer member onto the shaft member in the first die so that there is no interposing gap between the shaft member and the centrifugal impeller into which any blood can enter, wherein the spacer member includes a plurality of fan-shaped portions defining a plurality of blood flow paths;

removing the integrally-formed spacer member and shaft member from the first die;

affixing a plurality of magnets on the spacer member;

supporting the shaft member and spacer member in a second die;

insert molding a cover member onto the shaft member and the spacer member in the second die for enclosing the blood flow paths and the magnets, wherein the spacer member and cover member is each comprised of a respective material having a respective hardness lower than the first hardness;

fabricating a housing comprised of a two-part hollow body having a blood inlet and a blood outlet, wherein the blood inlet communicates with a chamber of the hollow body for an inflow of blood, wherein the blood outlet communicates with the chamber for an outflow of blood, and wherein the hollow body has a bearing configured to receive the shaft member; and assembling and affixing the two-part hollow body with the centrifugal impeller being encased within the chamber and the shaft member being rotatably received in the bearing.

7. The method of manufacturing a centrifugal pump according to claim 6, wherein the shaft member has a rod shape.

8. The method of manufacturing a centrifugal pump according to claim 6, wherein the shaft member is made of a metal material and the centrifugal impeller is made of a resin material.

9. The method of manufacturing a centrifugal pump according to claim 6, wherein the respective material of the spacer member and the cover member is comprised of thermoplastic, and wherein the step of insert molding the cover member onto the shaft member is comprised of:

injecting the thermoplastic in liquid form into the second die and surrounding a portion of the shaft member; and cooling the thermoplastic in the die to solidify the cover member on the shaft member.

* * * * *